United States Patent
Fitzgerald et al.

(10) Patent No.: US 12,332,252 B2
(45) Date of Patent: Jun. 17, 2025

(54) GFAP ACCUMULATING IN STROKE

(71) Applicants: Randox Laboratories Ltd., Antrim (GB); Randox Teoranta, Donegal (IE)

(72) Inventors: Stephen Peter Fitzgerald, Crumlin Antrim (GB); Ivan McConnell, Crumlin Antrim (GB); Ciaran Richardson, Donegal (IE); John Lamont, Crumlin Antrim (GB); Konstantinos Makris, Athens (GR)

(73) Assignees: Randox Laboratories Ltd., Crumlin (GB); Randox Teoranta, Donegal (IE)

( * ) Notice: Subject to any disclaimer, the term of this patent is extended or adjusted under 35 U.S.C. 154(b) by 960 days.

(21) Appl. No.: 16/462,520

(22) PCT Filed: Nov. 20, 2017

(86) PCT No.: PCT/EP2017/079822
§ 371 (c)(1),
(2) Date: May 20, 2019

(87) PCT Pub. No.: WO2018/095872
PCT Pub. Date: May 31, 2018

(65) Prior Publication Data
US 2019/0346458 A1    Nov. 14, 2019

(30) Foreign Application Priority Data

Nov. 23, 2016  (GB) ..................... 1619823

(51) Int. Cl.
*G01N 33/53* (2006.01)
*G01N 33/68* (2006.01)
*G16H 50/30* (2018.01)

(52) U.S. Cl.
CPC . *G01N 33/6893* (2013.01); *G01N 2800/2871* (2013.01); *G16H 50/30* (2018.01)

(58) Field of Classification Search
CPC ....... G01N 33/6893; G01N 2800/2871; G16H 50/30
See application file for complete search history.

(56) References Cited

U.S. PATENT DOCUMENTS

2015/0247867 A1* 9/2015 Curdt ................. G01N 33/6896
                                                        514/789

FOREIGN PATENT DOCUMENTS

WO     2014/195698 A1    12/2014
WO     2016/087611 A1     6/2016

OTHER PUBLICATIONS

Hermann et al (Restorative Neurology and Neuroscience 21 (2003) 177-190).*
Yuan et al. ( Zhongguo Xiandai Yixue Zazhi (2011), vol. 11, issue 6 pp. 627-632), Abstract).*
Vissers et al (Clinica Chimica Acta 366,2006,336-340.*
Dvorak et al. (Cerebrovasc Dis 2009;27:37-41.*
Rozanski Michal et al., "Glial Fibrillary Acidic Protein for Prehospital Diagnosis of Intracerebral Hemorrhage", Cerebrovascular Diseases, vol. 43, No. 1-2, Jan. 1, 2017, pp. 76-81.
Stricker, J., International Search Report and Written Opinion, PCT/EP2017/079822, European Patent Office, Mar. 15, 2018.
Xiong Lijun et al., "The use of serum glial fibrillary acidic protein test as a promising tool for intracerebral hemorrhage diagnosis in Chinese patients and prediction of the short-term functional outcomes", Neurological Sciences (Testo Stampato), vol. 36, No. 11, Jul. 21, 2015, pp. 2081-2087.

* cited by examiner

*Primary Examiner* — Carmencita M Belei
(74) *Attorney, Agent, or Firm* — Gavrilovich, Dodd & Lindsey LLP

(57) ABSTRACT

The disclosure describes the use of glial fibrillary acidic protein as a marker of pernicious stroke.

4 Claims, 3 Drawing Sheets

Pernicious: Ischemic died, haemorrhagic, haemorrhagic delayed. Non-pernicious: Ischemic resolved, TIA, stroke mimic. Lines represent medians with interquartile range.

Cut-off indicator:

- >0.160 ng/ml GFAP gives 44% sensitivity & 96% specificity giving a likelihood ratio of 10.06 (likelihood ratio represents how many times more likely you are to have a pernicious stroke if you have a positive test – the likelihood ratio equals the % sensitivity divided by [100% - % specificity]).

GFAP ACCUMULATING IN STROKE

CROSS REFERENCE TO RELATED APPLICATIONS

This application is a U.S. National Stage Application filed under 35 U.S.C. § 371 and claims priority to International Application No. PCT/EP2017/079822, filed Nov. 20, 2017, which application claims priority to Great Britain Application No. 1619823.6, filed Nov. 23, 2016, the disclosure of which are incorporated herein by reference.

BACKGROUND

Stroke is a leading cause of death worldwide and can be defined as the rapidly developing loss of brain function(s) due to interruption in the blood supply to the brain. According to the World Health Organization, 15 million people per annum suffer stroke world-wide with 5 million dying and a further 5 million being permanently disabled. An ischemic stroke (IS) results in the blood supply to the brain is decreased resulting in brain damage and occurs when a blood vessel becomes blocked, usually via a blood clot. This clot may form locally at an atherosclerotic plaque (thrombotic stroke) or alternatively may occur due to a travelling particle or debris that has originated from elsewhere in the bloodstream (embolic stroke). The transient ischemic attack occurs when blood supply to the brain is temporarily decreased. A TIA is diagnosed if symptoms are quickly resolved (within 24 hours with the individual returning to normal health. Haemorrhagic stroke (HS) is the accumulation of blood within the skull vault. A haemorrhagic stroke occurs when a weakened blood vessel ruptures. The stroke-related condition in which an individual presenting with IS transforms at a later time point to HS, is termed 'Haemorrhagic transformation' (HT). Ischemic stroke accounts for approximately 85 percent of all stroke cases and haemorrhagic stroke 15 percent. The 30 day fatality rate for ischemic stroke is 8-12% and HS is 37-38%. In order to minimize neurological damage and death following stroke it is crucial that stroke patients are rapidly and accurately diagnosed so that appropriate treatment can be administered. For example, to breakdown clots anti-thrombolytic therapy such as tissue plasminogen activator (TPA) can be administered. However, such therapy is only warranted in IS and is detrimental in HS; the nature of TIA does not require such therapy and blood thinners such as warfarin and aspirin are prescribed in such cases. Haemorrhagic transformation can occur as part of the natural evolution of IS or as a result of anticoagulant or thrombolytic therapy in the acute phase of IS. This poses a serious problem to both the stroke-affected individual and the clinician with respect to decisions on anti-thrombolytic and anti-coagulative therapy use. Thus patients admitted to a clinic with stroke-like symptoms present the clinician with a highly complex differential diagnosis task. A clinician who upon confronting a patient suspects stroke must delineate the various stroke-like conditions-stroke mimics (hypoglycemia, drug overdose, migraine, seizures, hyponatremia, loss of consciousness, intracranial tumours, subdural hematoma, hypertensive encephalopathy, encephalitis/meningitis), transient ischemic attacks, ischemic strokes, haemorrhagic strokes and strokes that transform into haemorrhagic stroke, and a wrong diagnosis could have fatal consequences. At present if stroke is suspected, physical symptoms are evaluated and a CT scan is usually performed. A CT scan has good sensitivity for identifying HS patients (approximately 90% sensitivity) but has poor sensitivity for the detection of IS. The detection of stroke-related biomolecules (biomarkers) in biological fluids are a potential supportive means of stroke diagnosis. Biomarkers have the potential to expedite and increase the accuracy of stroke diagnosis. Various candidate biomarkers have been proposed for diagnosis of stroke (EP1238284; WO 2010/086697; WO 2010/012834; WO 2002/012892), while EP1419388 discloses data that distinguishes IS from HS and all stroke types from non-stroke controls. The utility of glial fibrillary acidic protein (GFAP) as a biomarker of HS is becoming increasingly recognized. Standard treatment for ischemic stroke is thrombolytic and anti-coagulative therapy. Such therapy is, however, detrimental to an individual suffering from HS or who is a potential HS transformer. Biomarkers of HS transformation, preferably identifiable within 24 hrs of admission of stroke patients, could contribute to clinical procedures to manage and minimize the impact of bleeding in the brain. WO2006/036220 provides data for the use of the biomarkers cellular fibronectin (cFn) and metalloproteinase-9 (MMP-9) in the context of HS transformation; Foerch et al (2007) describe S100B as a risk factor of HS transformation following thrombolytic therapy in acute stroke; Kim et al (2014) describe a particular time-course of neuron-specific-enolase concentration as being associated with HS transformation; Zhongping (2011-Abstract) describe the relationship between glial fibrillary acidic protein (GFAP) and non-thrombolytic HS transformation. Despite previous and ongoing research into biomarkers for prediction of HS transformation in stroke patients there are no biomarker assays in use in hospitals to address this problem.

REFERENCES

Foerch et al (2007). Stroke, 38(9):2491-5.
Kim et al (2014). Journal of Stroke and Cerebrovascular Diseases, 23(9):2437-2443.
Zhongping A N (20011). Chinese Journal of Contemporary Neurology and Neurosurgery, 11(6): 627-632.

SUMMARY OF INVENTION

Described are methods of supporting the prediction of the course of an ischemic stroke in a patient. The methods utilize the structural protein glial fibrillary adipocyte (GFAP) and brain imaging to identify normal ischemic patients and ischemic patients at risk of haemorrhagic transformation. During the study to gauge the use of GFAP to predict the evolution of an ischemic stroke, it was surprisingly found that GFAP concentration was an indicator of fatal ischemic stroke. Based on these results, the invention describes methods for combining brain scanning and GFAP measurement in patients displaying stroke symptoms to support the discrimination of non-pernicious and pernicious pathologies thus enabling timely and accurate diagnoses, patient treatment prioritization and more efficient patient management.

DETAILED DESCRIPTION OF THE INVENTION

Figure 1:
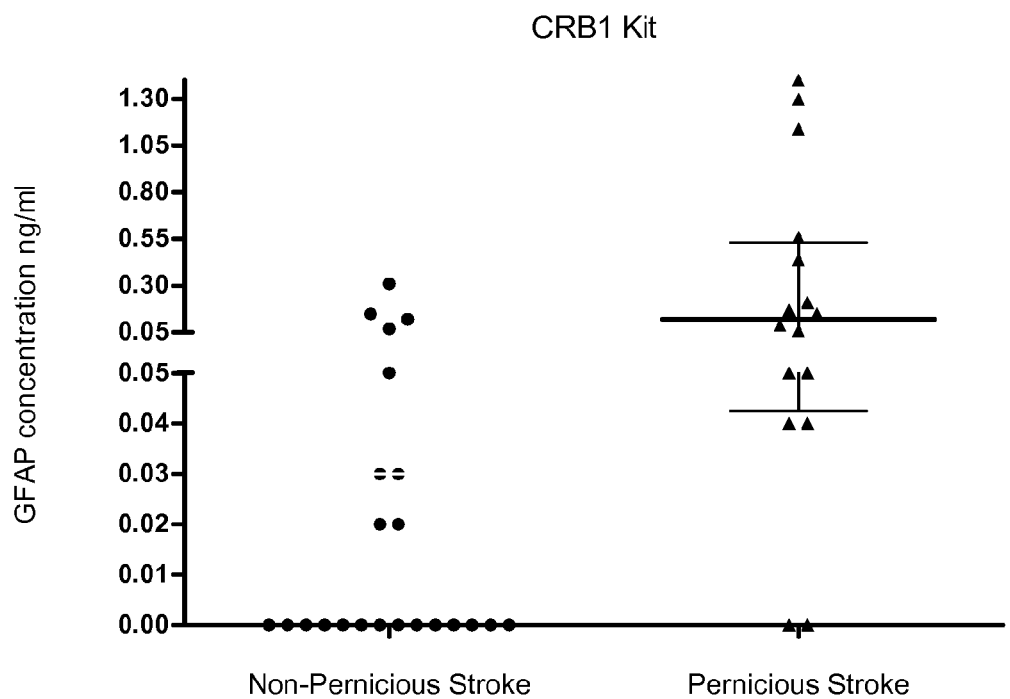
FIG. 1 Graph of pernicious vs non-pernicious stroke.
Figure 2:
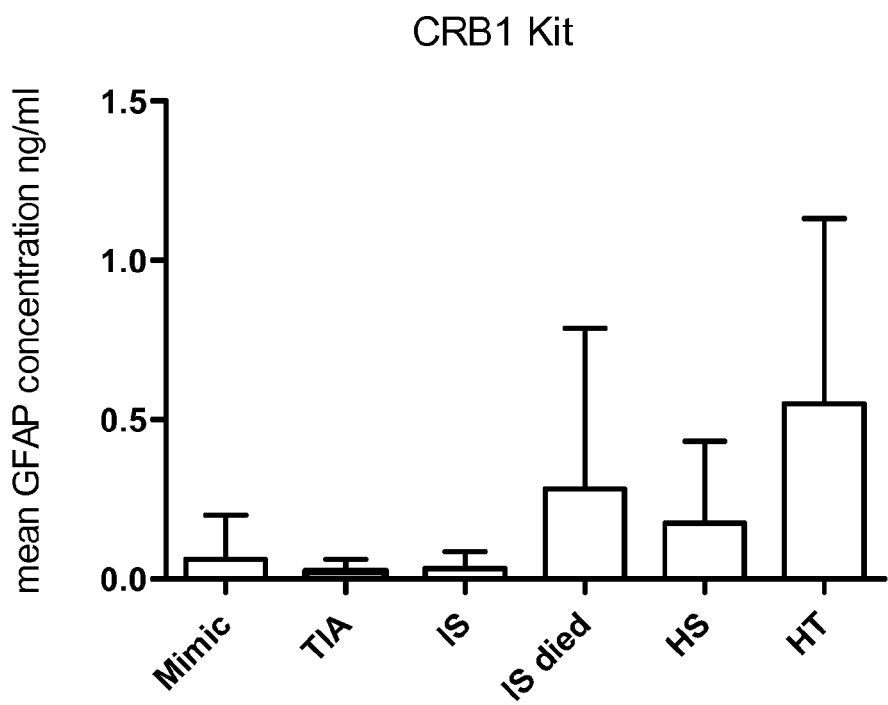
FIG. 2 Graph of stroke types for analyzed cohort (means with standard deviation bars).

The invention describes a method of predicting pernicious stroke in a suspected stroke patient comprising, within 24 hours of presentation, measuring the amount of glial fibrillary amyloid protein from a biological sample taken from the patient and subjecting the patient to a brain scan and, if glial fibrillary amyloid protein value is normal and the brain scan negative for haemorrhagic stroke at >24 hours from admission taking a further sample from the patient and measuring the amount of glial fibrillary amyloid protein, in which [0010] high glial fibrillary amyloid protein level and a brain scan positive for haemorrhagic stroke on admission indicates haemorrhagic stroke [0011] a high glial fibrillary amyloid protein level and a brain scan negative for haemorrhagic stroke on admission indicates fatal ischemic stroke [0012] a normal glial fibrillary amyloid protein level and brain scan negative for haemorrhagic stroke on admission and a high glial fibrillary amyloid protein level after 24 hours indicates haemorrhagic transformation By supporting the identification of the pernicious stroke sub-type as well as aiding the delineation of non-pernicious and pernicious strokes, the method enables the clinician to be more informed regarding the most appropriate treatment and management regime for the patient. For example, a high glial fibrillary amyloid protein level and a brain scan negative for haemorrhagic stroke on admission could support a decision by the clinician to administer a clot busting drug such as tissue plasminogen activator, a normal glial fibrillary amyloid protein level and brain scan negative for haemorrhagic stroke on admission and a high glial fibrillary amyloid protein level after 24 hours would support a decision to closely monitor the patient for haemorrhagic stroke transformation. The second glial fibrillary amyloid protein measurement is preferably taken at 24-96 hours, preferably at 24-48 hours, from admission to the hospital or clinic or from symptom onset. In a preferred embodiment, a glial fibrillary amyloid protein level 22 times, preferably ≥3 times, most preferably 4 times greater than a healthy control value or a non-pernicious stroke value is indicative of pernicious stroke. In the methods and examples of the studies this normally corresponds to a glial fibrillary amyloid protein level greater than a value within the range of 0.140-0.180 and 0.165-0.205 ng/ml being indicative of pernicious stroke. Thus a preferred embodiment of the method has the higher GFAP level that is indicative of pernicious stroke greater than a value within the range of 0.140-0.205 ng/ml and preferably greater than a value within the range of 0.165-0.205 ng/ml. The application of a cut-off range helps mitigate inherent user and equipment variation associated with the handling and analysis of samples. Furthermore, it is also well understood in the art that normal or background biomarker concentrations may exhibit slight variation due to, for example, age, gender or ethnic/geographical genotypes. As a result, the cut-off range or value used in the methods of the invention may also slightly vary due to optimization depending upon the target patient/population. Whatever cut-off range or value is applied in the methods of the invention make use of the finding that a higher than normal GFAP level indicates pernicious stroke.

A further aspect of the invention is a method of predicting fatal ischemic stroke in a suspected stroke patient comprising, within 24 hours of presentation, measuring the amount of glial fibrillary amyloid protein from a biological sample taken from the patient and subjecting the patient to a brain scan, in which a level higher than normal of glial fibrillary amyloid protein and a brain scan that is negative for haemorrhagic stroke is indicative that the patient is at increased risk of fatal ischemic stroke. A level higher than normal of glial fibrillary amyloid protein in the patient can be gauged by comparing the higher level value to that of a control sample, the control sample being a healthy patient, a healthy population of patients, or a patient or patients categorized as one or more of TIA, stroke mimic, or non-pernicious ischemic stroke.

The brain scan can be effected using any analytical instrument and/or technique capable of identifying stroke e.g. computerized tomography, an adapted form of computerized tomography, magnetic resonance imaging etc.

The invention further describes a method of treatment of fatal ischemic stroke comprising measuring the level of glial fibrillary amyloid protein from a biological sample taken from the patient taken upon presentation and subjecting the patient to a brain scan in which a higher than normal level of glial fibrillary amyloid protein upon presentation together with a brain scan negative for haemorrhagic stroke implies fatal ischemic stroke, and administering anti-thrombolytic therapy.

The invention describes a method of identifying patients with IS who are at risk of death or transforming to HS using a brain scan and the concentration of GFAP in a blood sample taken from the patient. The method incorporates taking a brain scan and a sample from the patient within 24 hours of the onset of stroke-like symptoms. In one embodiment, the glial fibrillary acidic protein measurement is taken ≤5 hours from admission or symptom onset. The method enables more informed therapeutic decisions to be made, especially enabling a more risk free administration of thrombolytic and anticoagulative drugs. For all methods of the invention a normal or control level of glial fibrillary amyloid protein corresponds to a level of GFAP that has been measured in a healthy patient (including a GFAP level measured in the patient undergoing stroke prior to the onset of stroke) or a healthy population of patients, or has been derived from a patient or a population of patients categorised as one or more of TIA, stroke mimic, or ischemic stroke. Healthy patient(s) in this context implies one not undergoing stroke. In the context of the patent, unless otherwise stated, ischemic stroke refers to ischemic stroke that is non-fatal ischemic stroke. Brain scan includes computerised tomography (CAT scan), X-ray, magnetic resonance imaging (MRI), ultrasound or any other machine-based (medical device) scan in which the interaction of the brain with wave or particle output from a medical device enables an abnormal brain event to be highlighted, an abnormal brain event being one which potentially injurious to the brain. In the context of the current invention, the abnormal brain event is a stroke, especially an ischemic or haemorrhagic stroke. CAT scan, MRI and their variants are the most prevalently used brain scanning techniques used for supporting stroke diagnosis. As used herein, the term 'ischemic stroke (IS)' refers to the type of stroke that occurs when blood supply to the brain is decreased, resulting in brain damage. An ischemic stroke occurs when a blood vessel becomes blocked, usually via a blood clot. This clot may form locally at an atherosclerotic plaque (thrombotic stroke) or alternatively may occur due to a travelling particle or debris that has originated from elsewhere in the bloodstream (embolic stroke). The term 'transient ischemic attack (TIA)' refers to a 'mini stroke' that occurs when blood supply to the brain is temporarily decreased. A TIA is diagnosed if symptoms are quickly resolved (within 24 hours with the individual returning to normal health). The term 'haemorrhagic stroke (HS)' occurs when blood accumulates within the skull vault, usually when a weakened blood vessel ruptures. Haemorrhagic stroke can be classified into two major sub-types: intracerebral (within the brain tissue); and subarachnoid (around the surface of the brain and under its protective layer). In the context of the current invention the use of the term 'predicting' is synonymous with the term 'predicting an increased risk of', unless otherwise stated. The terms "subject" and "patient" may be used interchangeably herein and refer to a mammal including a non-primate (e.g. a cow, pig, horse, dog, cat, rat and mouse) and a primate (e.g. a monkey and human). Preferably the subject or patient is a human. The term 'pernicious stroke' refers to the conditions haemorrhagic stroke, haemorrhagic transformation and ischemic stroke in which the patient is at high risk of death (fatal ischemic stroke). The term 'non-pernicious stroke' includes the conditions stroke mimic, transient ischemic attack and ischemic stroke, as well as other forms of stroke or stroke-like conditions in which a clinician would be of the opinion that the condition is not immediately life threatening. A standard value refers to any statistic that incorporates a measure of central tendency such as the mean and median. As used herein, the term 'biomarker' refers to a molecule present in a biological sample obtained from a patient, the concentration of which in said sample may be indicative of a pathological state. Various other biomarkers that have been found to be useful in differentiating between different stroke sub-types, either alone or in combination with other diagnostic methods, or as complementary biomarkers in combination with other biomarkers, can be used in conjunction with GFAP. As used herein, the term 'complementary biomarker' refers to a biomarker that can be used in conjunction with other stroke biomarkers to support diagnosis. The biological sample obtained from a patient is preferably a blood, serum or plasma sample. As used herein, the term 'ex vivo' has its usual meaning in the art and refers to a sample that has been removed from a patient's body. When a blood sample is taken from the patient for analysis, whole blood, serum or plasma is analysed. Analysis of the blood sample can be by way of several analytical methodologies such as mass spectrometry linked to a pre-separation step such as chromatography. The preferred methodology is based on immuno-detection. Immuno-detection technology is also readily incorporated into transportable or hand-held devices for use outside of the clinical environment. A quantitative immunoassay such as a Western blot or ELISA can be used to detect the amount of protein. A preferred method of analysis comprises using a multi-analyte biochip which enables several proteins to be detected and quantified simultaneously. 2D Gel Electrophoresis is also a technique that can be used for multi-analyte analysis. The purpose of the method of the invention is to identify which stroke sub-type the patient is suffering from, or has suffered, so that appropriate treatment can be administered. Therefore, in one embodiment, the method of the invention comprises a further step of administering appropriate treatment to the patient, once a differential diagnosis of the stroke sub-type has been made. For example, if as a result of carrying out the method of the invention it is determined that the patient has suffered, or is suffering, an IS, appropriate treatment such as thrombolytic therapy (e.g. tissue plasminogen activator (TPA)) can be administered to break-down clots. This may be administered in conjunction with other appropriate therapies, as determined by a physician. If as a result of carrying out the method of the invention it is determined that the patient has suffered, or is suffering, a TIA, blood thinners such as warfarin and aspirin may be prescribed and administered. If as a result of carrying out the method of the invention it is determined that the patient has suffered, or is suffering, a HS then these patients would typically be sent to a surgical unit to repair the damaged blood vessels.

Statistical Analysis

The cut-off concentrations or values are usually derived using statistical techniques. A standard method of biomarker statistical analysis is to use univariate methods to compare biomarker levels in various groups and highlight those biomarkers whose concentrations significantly differ across and between particular groups. This is followed by Receiver Operator Characteristic (ROC) analysis. The ROC curve is a preferred method of assessing a diagnostic test's accuracy; it addresses both the sensitivity, the number of true positives, and the specificity, the number of false positives, of the test. If two or more biomarkers are to be used in the IS diagnostic method i.e. GFAP and one or more biomarkers including DNA, RNA and protein based markers, a suitable mathematical model, such as logistic regression equation, can be derived. The logistic regression equation might include other variables such as age and gender of patient. The ROC curve can be used to assess the accuracy of the logistic regression model. The logistic regression equation can be used independently or in an algorithm to aid clinical decision making. The skilled person will be aware of numerous suitable methods for developing statistical algorithms, and all of these are within the scope of the present invention. Examples of suitable classification algorithms include multinominal logistic regression, multilayer perceptron neural network (MLP), artificial neural networks, support vector machines and random forest classifiers. To acquire a defined sensitivity and specificity the two conditions non-pernicious stroke and pernicious stroke must be demarcated using a suitable metric and this requires a reference value to be acquired for the 'normal condition', in this case the non-pernicious cohort. The normal condition could also be a healthy cohort. The reference value could be a pre-defined cut-off value which achieves the optimal sensitivity and specificity values for the target condition, a median value, mean value, quartile value etc. The methodology and analyzer used to measure a biomarker in a biological sample inevitably results in the concentration value of a particular biomarker varying. Thus, although the cut-off value, mean value etc used to determine risk of a non-pernicious or pernicious condition in a suspected stroke patient will probably vary slightly from platform to platform e.g. for an immunoassay slight variation due to, for example, the antibody (monoclonal, polyclonal etc.) or substrate (bead, elisa plate, biochip etc.), the core idea that the concentration level of GFAP as a biomarker for this purpose is valid and independent of the platform and methodology used in the analytical process.

Methods, Examples and Results

Patient Group

The study consisted of 39 patients displaying stroke symptoms admitted to the Emergency Department of KAT General Hospital, Athens, Greece. Patients were classified on admission using clinical analysis incorporating the Scandinavian stroke scale and by CAT scan. Blood samples were taken at the time of admission, at 24 hrs following admission, and every 24 hours thereafter up to day six except for patients who were diagnosed as TIA and stroke mimics who were subject to a single blood sample draw on admission. The time from the onset of stroke symptoms and hospital admission was <6 hours. Exclusion criteria included patients who were admitted to hospital >6 hours from the time of onset of stroke symptoms, patients with hepatic or renal pathologies and patients who had previously experienced a stroke.

Sample Analysis

EDTA plasma samples of blood obtained from the patients of the study group was tested for GFAP. The proteins were detected and quantified using biochips incorporating GFAP-specific antibodies and the Evidence Investigator (Randox Laboratories Ltd, Crumlin, UK) using the Cerebral 1 biochip (EV3573 Randox Laboratories Ltd, Crumlin, UK) according to instructions provided with the kit.

Results

Figure 3:
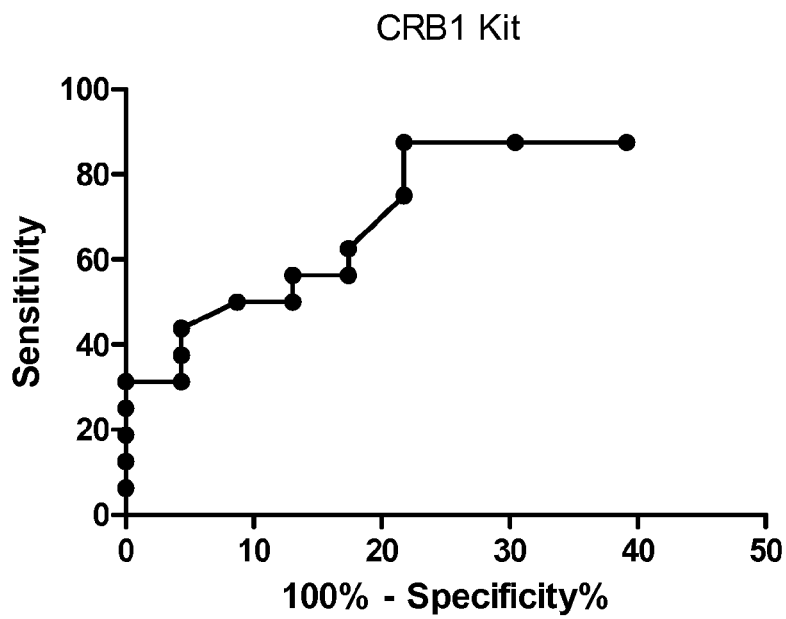
FIG. 3 ROC curve of pernicious vs non-pernicious stroke.

Pernicious and non-pernicious stroke cohorts were compared using ROC curve analysis. The results are shown in Table 1 and FIG. 3.

TABLE 1

Statistical measures of GFAP levels

| Condition | Sample number | Concentration (ng/ml) <24 hr | | | |
|---|---|---|---|---|---|
| | | Median | Average | P-value | AUC |
| CRB1 kit | | | | | |
| Non-pernicious stroke | N = 23 | 0.000 | 0.034 | | |
| Pernicious stroke | N = 16 | 0.120 | 0.356 | 0.0004 | 0.833 |

The immunoassay kit provides a sensitivity of 44% and specificity of 96% at a GFAP cut-off concentration of 0.160 ng/ml.

The invention claimed is:

1. A method for diagnosis and treatment comprising:
   (a) obtaining a first biological sample from a suspected pernicious stroke patient at admission, wherein the patient is admitted <6 hours from symptom onset, wherein the biological sample, is blood, serum or plasma;
   (b) measuring a first amount of glial fibrillary acidic protein (GFAP) in the first biological sample;
   (c) subjecting the patient to a brain CT scan (CT scan) on admission;
   (d) diagnosing the patient as having fatal ischemic stroke or hemorrhagic transformation comprising:
      (i) identifying the patient as having fatal ischemic stroke when (1) the first amount of GFAP is at least 2-fold higher than a normal control level, wherein the normal control level is the level of GFAP measured in a population of patients comprising non-fatal ischemic stroke patients or a value within a range of 0.140 ng/ml to 0.205 ng/ml, and (2) the CT scan is negative for hemorrhagic stroke, and
      (ii) identifying the patient as having non-fatal ischemic stroke undergoing hemorrhagic transformation when the amount of GFAP in the first sample has the normal control level and the CT scan is negative for hemorrhagic stroke at admission, and the method further comprises measuring a second amount of GFAP in a further biological sample taken from said patient at ≥24 hours from admission or symptom onset, wherein a higher level of the second amount of GFAP in the second sample than the first level of GFAP measured in the patient identified as having fatal ischemic stroke of (i), is indicative of hemorrhagic transformation; and
   (e) treating the diagnosed patient of (d) comprising administering a therapy, wherein the therapy for the identified patient of (i) is selected from the group consisting of an anti-thrombolytic therapy, anti-coagulative therapy or combination, and the therapy for the patient of (ii) comprises administering surgical repair of a damaged blood vessel.

2. The method of claim 1 in which the second amount of glial fibrillary acidic protein measurement from said further biological sample is taken at 24-96 hours from admission or from symptom onset.

3. The method of claim 1 in which the first amount of B glial fibrillary acidic protein measurement is taken s 5 hours from symptom onset, wherein the measurement is of the biological sample.

4. The method of claim 1, wherein the value is between 0.165-0.205 ng/ml.

* * * * *